(12) United States Patent
Ries

(10) Patent No.: US 9,101,369 B2
(45) Date of Patent: Aug. 11, 2015

(54) SURGICAL INSTRUMENT FOR DETACHABLY CONNECTING A HANDPIECE TO A SURGICAL TOOL

(75) Inventor: Wolfgang Ries, Linkenheim-Hochstetten (DE)

(73) Assignee: JOIMAX GMBH, Karlsruhe (DE)

( * ) Notice: Subject to any disclaimer, the term of this patent is extended or adjusted under 35 U.S.C. 154(b) by 32 days.

(21) Appl. No.: 13/515,609

(22) PCT Filed: Dec. 16, 2010

(86) PCT No.: PCT/EP2010/007715
§ 371 (c)(1),
(2), (4) Date: Jun. 13, 2012

(87) PCT Pub. No.: WO2011/076364
PCT Pub. Date: Jun. 30, 2011

(65) Prior Publication Data
US 2012/0253330 A1 Oct. 4, 2012

(30) Foreign Application Priority Data
Dec. 23, 2009 (DE) ............... 20 2009 017 470 U

(51) Int. Cl.
| | |
|---|---|
| *A61B 17/00* | (2006.01) |
| *A61B 17/32* | (2006.01) |
| *A61B 1/00* | (2006.01) |
| *A61B 17/16* | (2006.01) |
| *A61B 19/00* | (2006.01) |

(52) U.S. Cl.
CPC ............... *A61B 17/162* (2013.01); *A61B 17/00* (2013.01); *A61B 19/22* (2013.01); *A61B 19/2203* (2013.01); *A61B 2019/2242* (2013.01)

(58) Field of Classification Search
CPC ............... A61B 19/22; A61B 19/2203; A61B 2019/2242; A61B 17/00; A61B 17/162
USPC ........................ 606/1, 170; 600/107
See application file for complete search history.

(56) References Cited

U.S. PATENT DOCUMENTS

| | | | | |
|---|---|---|---|---|
| 5,490,683 | A | * | 2/1996 | Mickel et al. .................. 279/75 |
| 5,569,163 | A | * | 10/1996 | Francis et al. ................ 600/133 |
| 5,741,263 | A | | 4/1998 | Umber et al. |
| 5,871,493 | A | | 2/1999 | Sjostrom et al. |
| 6,139,214 | A | * | 10/2000 | Zirps et al. ..................... 403/325 |
| 6,328,752 | B1 | | 12/2001 | Sjostrom et al. |
| 6,595,984 | B1 | * | 7/2003 | DeGuillebon .................... 606/1 |
| 7,226,460 | B2 | | 6/2007 | Gibson et al. |
| 8,419,760 | B2 | | 4/2013 | Wiebe, III |
| 2001/0039427 | A1 | * | 11/2001 | Dinger et al. ................. 606/167 |
| 2002/0026202 | A1 | * | 2/2002 | Honey et al. .................. 606/127 |
| 2005/0165277 | A1 | * | 7/2005 | Carrillo et al. ................ 600/154 |

(Continued)

FOREIGN PATENT DOCUMENTS

| | | |
|---|---|---|
| CN | 2232727 Y | 8/1996 |
| CN | 101420912 A | 4/2009 |

(Continued)

*Primary Examiner* — Lynsey Crandall
*Assistant Examiner* — Sebastian X Lukjan
(74) *Attorney, Agent, or Firm* — McGlew and Tuttle, P.C.

(57) ABSTRACT

Surgical instrument with a handpiece having a drive and with a surgical tool, which has a tube and a working part with a shaft and with a tool head, the tube of the surgical tool can be detachably connected to the handpiece by a first coupling part and the shaft of the working part can be detachably connected to a drive shaft in the form of a pin of the drive by a second coupling part simultaneously.

13 Claims, 4 Drawing Sheets

(56) References Cited

U.S. PATENT DOCUMENTS

| | | |
|---|---|---|
| 2007/0021766 A1 | 1/2007 | Belagali et al. |
| 2008/0188848 A1 | 8/2008 | Deutmeyer et al. |
| 2009/0209946 A1* | 8/2009 | Swayze et al. .................. 606/1 |
| 2010/0076477 A1* | 3/2010 | Jezierski et al. ............ 606/180 |

FOREIGN PATENT DOCUMENTS

| | | |
|---|---|---|
| DE | 201 10 156 U1 | 11/2001 |
| DE | 69 622 563 T2 | 3/2003 |
| DE | 10 2006 062 421 A1 | 7/2008 |
| EP | 1 880 683 A1 | 1/2008 |
| EP | 1 938 757 A1 | 7/2008 |
| JP | H02-061317 | 8/1990 |
| JP | 2000-507840 A | 6/2000 |
| JP | 2006-043459 A | 2/2006 |
| JP | 2008-532712 A | 8/2008 |
| JP | 2008-543503 A | 12/2008 |
| WO | 2007/002230 A1 | 1/2007 |

\* cited by examiner

Fig. 2    Section A-A
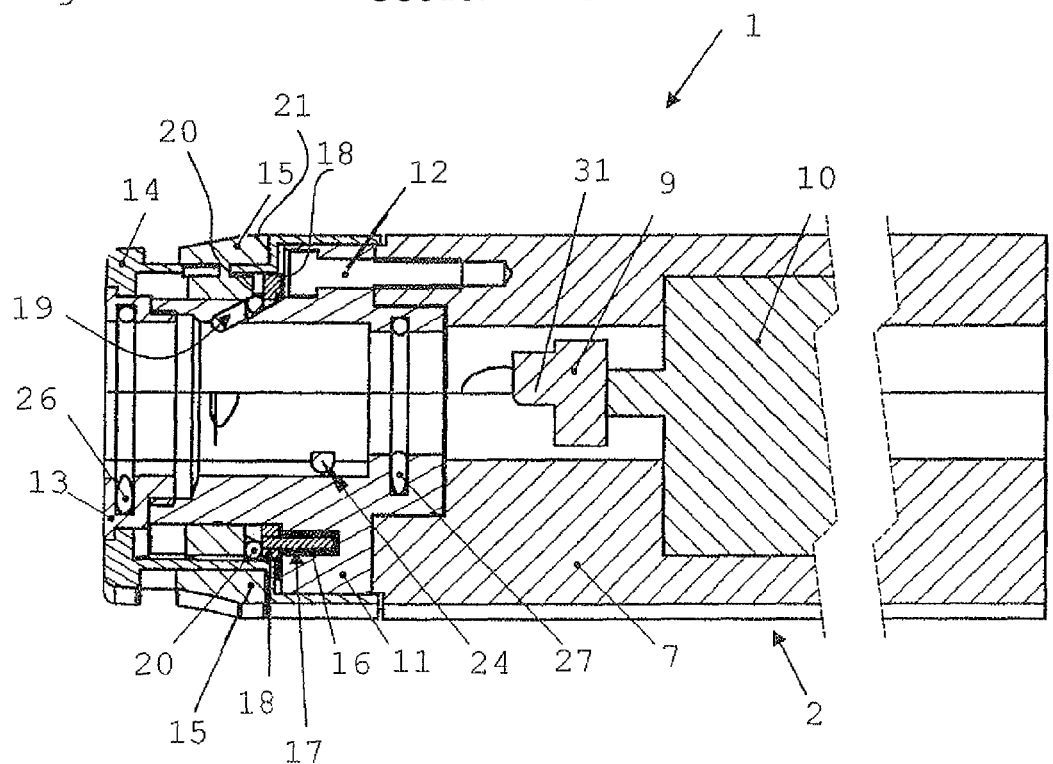
Fig. 3
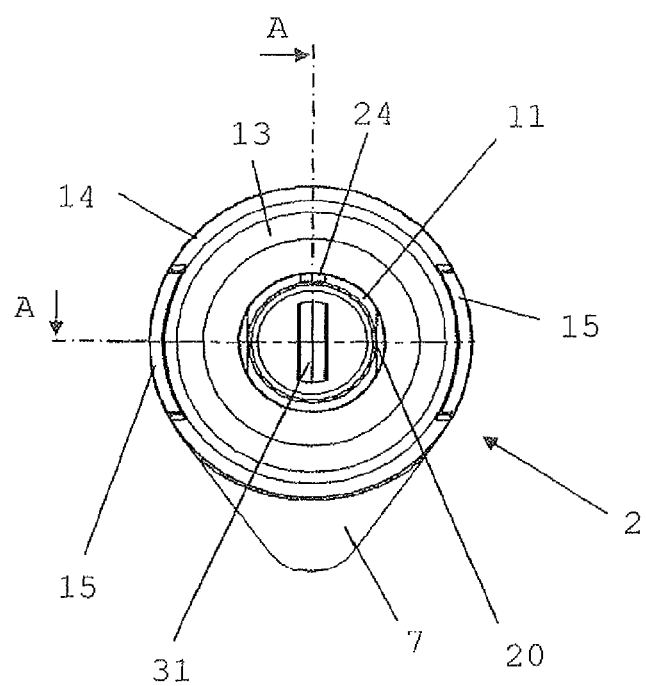

Fig. 4a
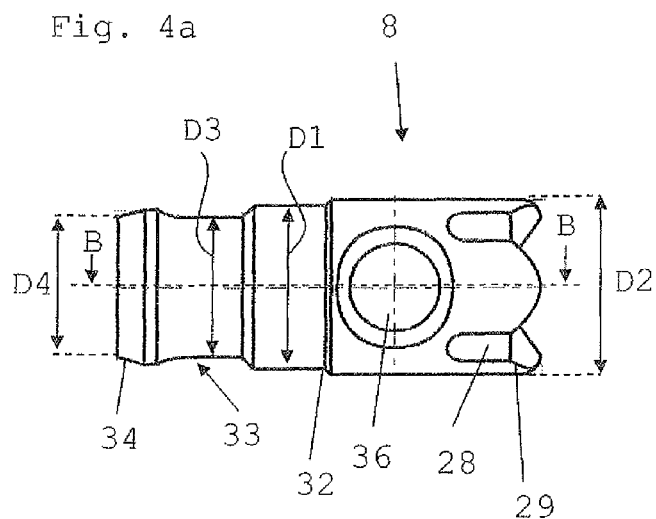
Fig. 4b
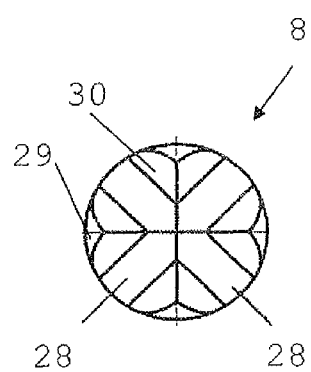
Fig. 4c   Section B-B
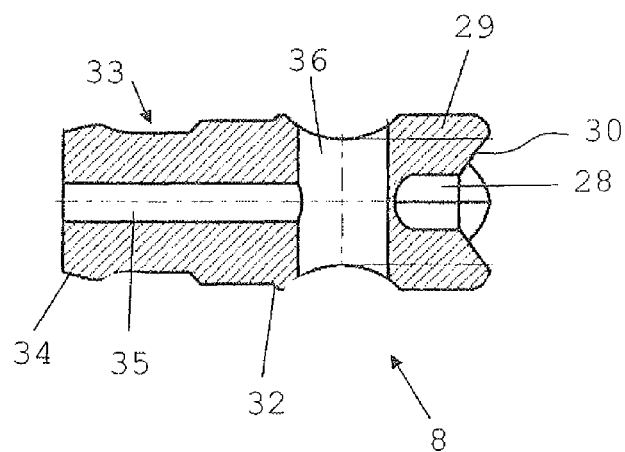

SURGICAL INSTRUMENT FOR DETACHABLY CONNECTING A HANDPIECE TO A SURGICAL TOOL

CROSS REFERENCE TO RELATED APPLICATIONS

This application is a U.S. National Phase application of International Application PCT/EP2010/007715 and claims the benefit of priority under 35 U.S.C. §119 of German Patent Application DE 20 2009 017 470.0 filed Dec. 23, 2009, the entire contents of which are incorporated herein by reference.

FIELD OF THE INVENTION

The present invention pertains to a surgical instrument with a handpiece having a drive and with a surgical tool.

BACKGROUND OF THE INVENTION

Surgical tools, which are inserted into a handpiece, are known in various embodiments. The handpieces are usually connected to a drive, so that the tools or partial areas of the surgical tools can be driven, e.g., set into rotation. Such surgical tools may be designed, for example, as tools for minimally invasive endoscopy, especially in the area of the spine.

It is known from the state of the art, e.g., from DE 10 2006 062 421 A1, that such a handpiece is provided with a central hole or recess, into which a coupling area or attachment area of the surgical tool is inserted. Corresponding drive couplings of the handpiece now come to mesh with coupling parts of the surgical tool, so that rotary drive is achieved. The surgical tool is inserted into and locked in a handpiece by the handpiece being provided with a tool mount, with which a locking element of the surgical tool can be caused to detachably mesh. Such a locking element may be designed, for example, in the form of a ring groove. The counterpiece of the locking element to the ring groove within the tool mount may be designed, for example, in the form of a hook, balls or the like. When inserting the surgical tool into the handpiece, locking or coupling can thus take place, which prevents the surgical tool from becoming accidentally separated from the handpiece during use. To remove the surgical tool from the handpiece, for example, an actuating means, e.g., a button or a slide, is to be actuated.

To guarantee optimal coupling between the surgical tool and drive, coupling parts in the form of grooves or cams, which mesh with a counterpiece of the drive, are formed at the end of the surgical tool. Such a coupling is known from DE 69 622 563 T2, wherein a surgical instrument has a quick-action coupling, which comprises a plug-in connection in the manner of a bayonet catch and a coupling pin proximally from the tool to be inserted.

However, the devices known from the state of the art often have a complicated design, are correspondingly costly, their manufacture is complicated and they often can be operated poorly under surgical conditions of use.

U.S. Pat. No. 5,741,263 shows a surgical instrument with a hand piece and tool with a double coupling mechanism, in which, however, a slide must be shifted simultaneously for inserting the tool in order to make the insertion of the tool possible at all. Such a double connection movement is a drawback and is undesired in the corresponding operating system.

U.S. Pat. No. 5,871,493, which is likewise of this class, likewise shows a surgical element, in which, however, the uncoupling mechanism at the tool is designed in the form of an actuating element. This makes the tool, on the one hand, complicated and expensive and thus it cannot be formed as a disposable tool; on the other hand, a difficult cleaning and disinfection possibility arises as a result of this and precisely in a multi-usable tool, which is connected with risks for the patient.

Finally, EP 1 880 683 shows a surgical element not of this class, in which a tool can be connected at an intermediate part, on the one hand, by a transversely insertable cross pin (which can get lost), and, on the other hand, a drive element can be inserted at the opposite end at best in a frictionally engaged, but not positive locking manner and thus these parts lie open jointly as rotary parts over the entire length, such that such an element can be used in an open cavity, such as a dental element in the oral cavity, with certainty but not as a surgical element through body openings, especially in minimally invasive procedures.

SUMMARY OF THE INVENTION

The basic object of the present invention is to provide a surgical instrument for coupling a surgical tool of the type mentioned in the introduction, which has a simple design, can be manufactured in a cost-effective manner and can be actuated reliably and in a simple manner.

To accomplish the above object, the invention includes a surgical instrument comprising a handpiece having a drive and a surgical tool, which has a tube and a working part with a shaft and a tool head. The tube of the surgical tool can be detachably connected to the handpiece by means of a first coupling part and wherein the shaft of the working part can be detachably connected to a drive shaft in the form of a pin of the drive by means of a second coupling part simultaneously. A mount in the handpiece receives the first coupling part of the surgical tool. The handpiece comprises two clamping pins displaceable in oblique grooves. The cross pins extend under spring action into an interior of the mount. The clamping pins are displaceable in the oblique grooves against the spring action during insertion of the surgical tool.

Provisions are made here in an especially preferable embodiment for the surgical tool to have a hollow cylindrical tube and a working part located therein with a shaft and with a tool head, wherein the working part is mounted rotatably, being specifically mounted in the shaft, so that the two are connected to one another, being specifically connected rotatably and are especially superimposed to each other. Furthermore, provisions are made in the present invention for the first coupling part to be arranged proximally at the tube of the tool and for the second coupling part to be mounted rotatably within the tube of the tool. Thus, only the working part is rotated by means of the second coupling part, which meshes with the drive shaft, rather than the complete tool being rotated during the use of the surgical instrument. The drive shaft of the drive now sets the working part of the surgical instrument into motion, e.g., into rotation, by means of the second coupling part. The detachable connection of a tube with a handpiece, which handpiece is not consequently rotating, wherein said detachable connection is separate from the working part, is used as a protection for the working part or the outside environment of the work area, e.g., delicate nerve tissue.

Provisions are made in an especially preferred embodiment for the handpiece to be of an essentially cylindrical design, wherein said handpiece has a grip with a mount for a tool and a clamping fastening means within the mount, and for a ring seal to be provided in the closing ring of the handpiece for sealing the mount of the tool. Furthermore, provisions are made in a preferred embodiment for an actuating slide being arranged at the handpiece, which said actuating slide is pressed by means of a ring-shaped pressing plate with at least one spring and preferably three or four springs, wherein said actuating slide is axially displaceable into a locked position and into a released position.

Reliable and fast locking of the surgical tool is achieved by the diameter of the tool mount being adapted to that of the replaceable surgical tools, which have a round tube with a first coupling part, which tube permits insertion with small clearance into the tool mount. Provisions are made in this connection in an especially preferred embodiment for the first coupling part to have a ring groove for fastening and locking proximally at the tool. In an especially preferred embodiment, a clamping fastening is provided for locking, in which case at least one clamping pin, located in elongated grooves milled radially obliquely into the inner wall of the mount, extend in a chord-like manner into the interior of the mount. The clamping pins are dimensioned here such that they mesh with the ring groove of the first coupling part in a positive-locking manner in a locked position.

To connect the surgical tool within the handpiece to the drive shaft of the drive, preferably of an electric motor, provisions are made for the second coupling part to be of an essentially cylindrical design with an axial hole and for the second coupling part to have radially a through hole, which is arranged at right angles to the axial hole and closes same. The shaft of the tool part can be inserted into the axial hole in a non-positive manner and/or by connection in substance.

Provisions are made in an especially preferred embodiment for at least two grooves, whose width and depth correspond to the shape of the elongated pin of the drive shaft, to be milled in the proximal end area of the second coupling part. Provisions are, furthermore, made to simplify the positioning of the second coupling part on the pin of the drive shaft for the cams formed by the milled grooves to have an axial edge towards the grooves. When the coupling part is inserted into the handpiece, the pin can slide into one of the two grooves of the second coupling part. This leads to fast and simple connection of the working part and drive shaft.

The diameter of the second coupling part is dimensioned such that a first diameter corresponds to the diameter of the surgical tool being used, the second coupling part can be inserted into this and the second coupling part has an axial bevel to facilitate the insertion of the second coupling part into the shaft of the surgical tool.

Provisions are, furthermore, made for a second diameter of the second coupling part to be larger than the first diameter, with a step to the first diameter, which step acts as a plug for the insertable tool, and for a third diameter of the second coupling part to be smaller than the first diameter, wherein a seal can be inserted into the cylindrical recess formed. These embodiments guarantee that the second coupling part can be pressed into the shaft of the surgical tool more simply and more reliably and is seated reliably on the drive shaft of the drive.

Provisions are made in an extremely preferred embodiment for at least one coupling part to consist of metal, preferably stainless steel, and for at least one other coupling part to consist of a multiphase plastic, which consists of a copolymer based on methacrylate and styrene, preferably containing butadiene. A coupling part consisting of this material can be manufactured in a simple manner, can be injected into a mold and has the further advantage that this material will be deformed during a sterilization process such that there is no fitting for the surgical tool used in a handpiece any longer, as a result of which the problem of cleaning and sterilization of these tools is eliminated altogether. An optimally sharp tool is thus ensured for each procedure performed on bones.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a partial longitudinal sectional view of a surgical instrument according to the present invention according to section A-A according to FIG. 3;

FIG. 3 is a front view of the opening into which the handpiece of the surgical instrument according to the present invention is inserted;

FIG. 4a is a side view of a second coupling part of the surgical instrument according to the present invention;

FIG. 4b is a front-side view of a proximal end of the second coupling part;

FIG. 4c is a longitudinal sectional view through the second coupling part along section B-B according to FIG. 4a.

DESCRIPTION OF THE PREFERRED EMBODIMENTS

Figure 1:
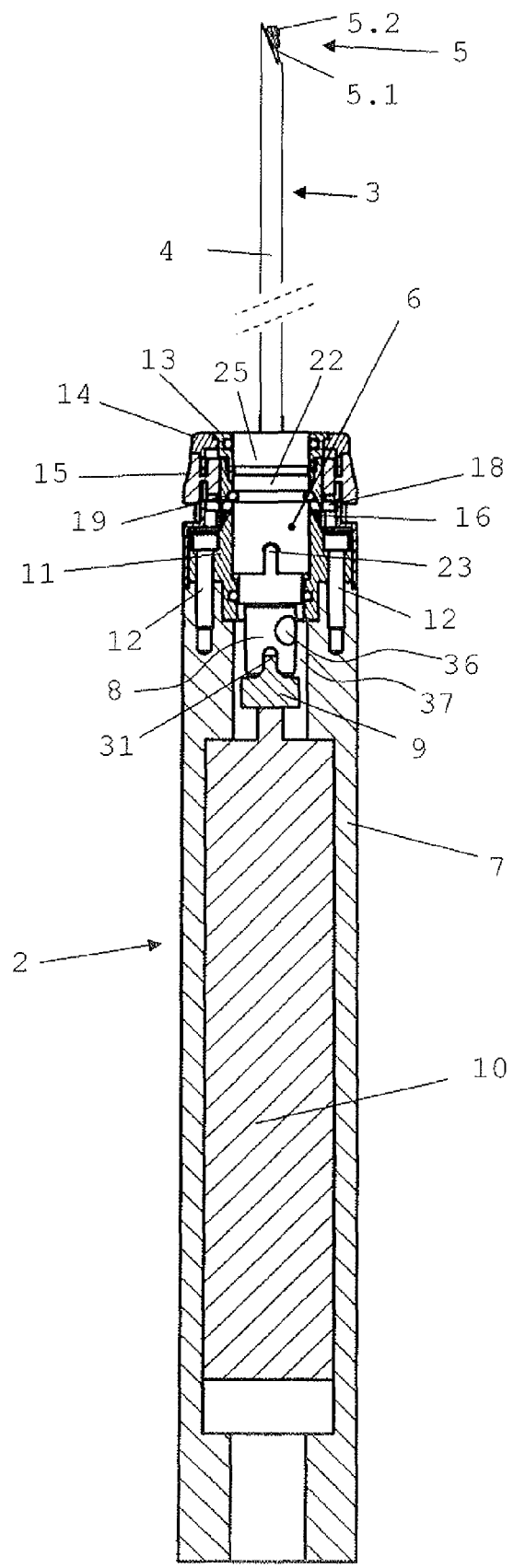
FIG. 1 is a longitudinal sectional view through a surgical instrument according to the present invention, wherein a tool is locked in a handpiece.

Referring to the drawings in particular, FIG. 1 shows a surgical instrument 1 according to the present invention in a longitudinal section. The surgical instrument 1 has an essentially cylindrical handpiece 2 made of stainless steel, into which a surgical tool 3, especially a bone cutter, can be inserted in a nondestructively detachable manner. Tool 3 has an outer cylindrical tube 4 and a working part 5 rotatable in this. Working part 5 is formed from a cylindrical shaft 5.1 and a tool head 5.2. Tube 4 can be connected to a mount 11 arranged at the outer cylindrical grip 7 of the handpiece 2 by means of the first coupling part 6. Working part 5 can be connected via a second coupling part 8 to a drive shaft in the form of a pin 31 of a drive 9 arranged in handpiece 2 and is at the same time mounted rotatably within tube 4. Drive 9 can be driven by a motor 10, preferably an electric motor.

The cylindrically shaped grip 7 of the handpiece 2 is connected to a likewise cylindrically shaped mount 11 by means of two fillister head screws 12. Handpiece 2 has a closing ring 13 provided with a thread and an end cap 14 surrounding same distally on the front side. An actuating lever 15 is axially displaceable along the outer edge of mount 11 against the action of springs 16, which are arranged each in a recess 17 within mount 11 (FIG. 2). Four springs 16 are provided in this embodiment located opposite each other in the housing of mount 11. The abutments of the springs 16 are located in the exemplary embodiment shown in FIGS. 1 and 2 proximally in the recess 17 of handpiece 2, on the one hand, and distally at an annular, movable pressing plate 18, on the other hand, so that springs 16 load and press this pressing plate 18 in the distal direction.

FIG. 2 shows another partial longitudinal section of the surgical instrument 1 along section A-A according to FIG. 3. Two clamping pins 20 are located in two opposite grooves 19 milled radially obliquely into the inner wall of mount 11, said clamping pins 20 extending in a locked position in a chord-like manner into the interior of mount 11. It can be seen that the spring-loaded pressing plate 18 is pressed by the springs 16 against the clamping pins 20. Actuating slide 15 is shown here in a released position, wherein said actuating slide 15 has a stop at a shoulder 21 of end cap 14.

FIG. 1 shows that the internal diameter of mount 11 is selected to be such that replaceable surgical tools 3, whose round tube 4 has a first coupling part 6 made of metal and is attached in a non-positive manner and/or by connection in substance, can be inserted into mount 11 with a small clearance. A coupling part 6 made of metal is used for secure guiding and fastening within the mount. The first coupling part 6 is of a cylindrical design and has a circular ring groove 22, with which the clamping pins 20 mesh in a locked position. To guarantee joint rotation of tube 4 and proper fitting of the tool 3 within the handpiece 2, a guide slot 23, which meshes via a rotation prevention means 24 within mount 11, is, furthermore, provided proximally at the first coupling part 6. The first coupling part 6 has another circular groove 25, which can be provided with a colored ring in order to better distinguish the surgical tools 3. To guarantee sealing of the surgical tool 3 being used within the handpiece 2, ring seals are provided at two positions. On the one hand, a ring seal 26 is provided in the closing ring 13 in handpiece 2 to seal mount 11 of tool 3 towards the outside. On the other hand, another ring seal 27 is arranged within mount 11 to seal the first coupling part 6 towards the drive 9.

FIGS. 4a through 4c show a preferred embodiment of the second coupling part 8 that can be inserted into tube 4. The second coupling part 8 shows a cylindrical shape and consists of plastic, said plastic containing at least one part of methacrylate-styrene and a percentage of butadiene. FIG. 4a shows here a side view of the second coupling part 8, which shows, as is also described in the front-side view 4b, two grooves 28 cut crosswise. As is shown in the front view in FIG. 4b, the grooves 28 extend at right angles to one another. The cams 29 formed hereby have, furthermore, beveled edges 30, which guarantees easy attachment of the second coupling part 8 to the drive shaft in the form of a pin 31. The second coupling part 8 has a first diameter D1, which is selected to be such that it corresponds to the internal diameter of a coupling part 6 of a tool 3 being used and the second coupling part 8 can thus be inserted into this coupling part 6. Furthermore, a second diameter D2 is provided, which is larger than the first diameter D1, and a step 32 in relation to the first diameter D1 acts as a stop for the surgical tool 3 that can be inserted. A third diameter D3 of the second coupling part 8 is, furthermore, made smaller than the first diameter D1, and, for example, a seal can be received in the cylindrical recess 33 formed. The second coupling part 8 has distally an axial bevel 34, which is designed such that it drops from a first diameter D1 to a fourth diameter D4, to facilitate insertion of the second coupling part 8 into coupling part 6 of the surgical tool 3. Furthermore, two holes extending at right angles to one another are provided in the interior of the second coupling part 8, an axial hole 35 being perforated by a radial through hole 36, as is shown in FIG. 4c. Furthermore, bone material cut off can be suctioned via both. A cross hole extends for this through the wall of grip 7 and the cavity 37, and a suction tube, via which suctioning is then performed, can be connected to said cross hole. The axial hole 35 is used to receive shaft 5.1 of the surgical tool 3.

Figure 5:
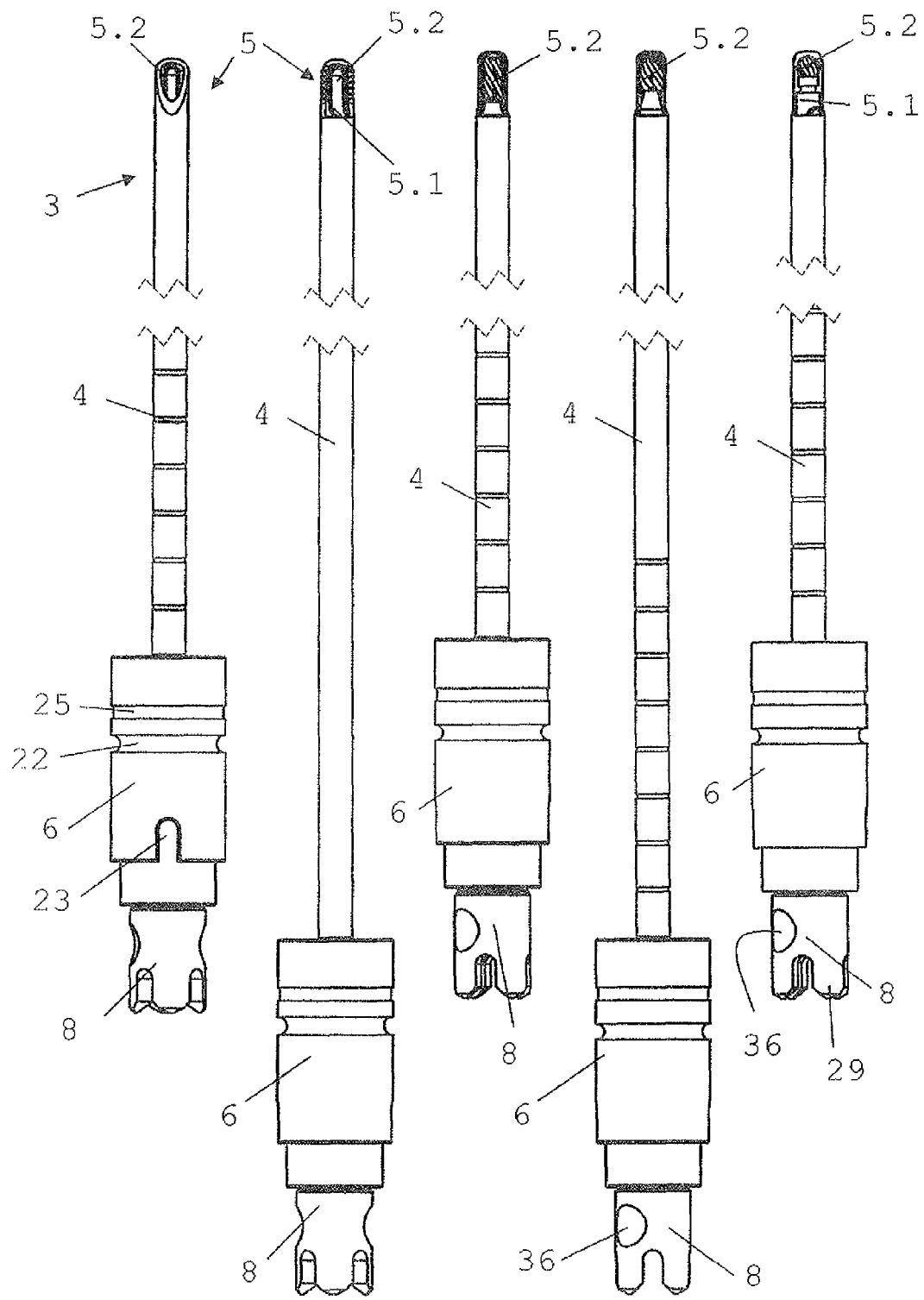
FIG. 5 is a view of a set of surgical tools for use with the surgical instrument according to the present invention.

FIG. 5 shows as an example a set of surgical tools 3, especially cutters or drills for spinal surgery, with a tube 4 each with a distally attached, first coupling part 6 and with a rotatable working part 5 arranged within tube 4 with a shaft 5.1, whose distal end is rigidly connected within a second coupling part 8 (optionally extrusion-coated). The second coupling part 8 is mounted here rotatably within tube 4. A plurality of different surgical tools 3 can be used for the surgical instrument 1 according to the present invention due to the combination of these coupling parts.

A corresponding surgical tool 3 is used with the handpiece 2 as follows:

The surgical tool 3 is carefully inserted into mount 11 of the handpiece 2. The clamping pins 20 are now moving within their grooves 19 in the direction of pressing plate 18 and the pressing plate 18 is displaced proximally against the spring action of the springs 16.

The first coupling part 6 is inserted further into mount 11 of handpiece 2 and slightly rotated in the process, so that the guide slot 23 of the first coupling part 6 is pushed over the rotation prevention means 24. At the same time, a slight rotation of tool 3 causes the second coupling part 8 to be pushed over pin 31 by means of one of the grooves 28 and thus to mesh with the drive shaft 9. If the second coupling part 8 is seated properly on pin 31, the ring groove 22 and clamping pins 20 are at the same level, so that these can mesh with the ring groove 22 of the first coupling part 6. Pressing plate 18 is displaced distally in the forward direction by the spring loading of springs 16. As a result, the actuating slide 15 is displaced under spring action into a locked position axially in the direction of the distal end of handpiece 2. To sever the connection, the actuating slide 15 is displaced into an open position axially in the direction of handpiece 2, and the actuating slide 15 displaces the pressing plate 18 and hence the springs 16 likewise in the proximal direction and compresses same. The clamping pins 20 are now being moved within their grooves 19 in the direction of pressing plate 18 and release the path for the removal of the surgical tool 3. The double coupling of a surgical tool 3, in which case a clamping pin fastening grips, on the one hand, a first coupling part of a tube 4 of a surgical tool 3 and, on the other hand, a second coupling part 8 guarantees a rotatable connection between a shaft 5.1 of a working part 5 and a drive shaft in the form of a pin 31 of a drive 9, ensures secure coupling between a surgical tool and a corresponding handpiece 2.

While specific embodiments of the invention have been shown and described in detail to illustrate the application of the principles of the invention, it will be understood that the invention may be embodied otherwise without departing from such principles.

The invention claimed is:

1. A surgical instrument, comprising:
   a handpiece having a drive; and
   a surgical tool, which has a tube and a working part with a shaft and a tool head, wherein the tube of the surgical tool can be detachably connected to the handpiece by means of a first coupling part and wherein the shaft of the working part can be detachably connected to a drive shaft in the form of a pin of said drive by means of a second coupling part simultaneously, wherein a mount in said handpiece receives said first coupling part of the surgical tool, said handpiece comprising two clamping pins displaceable in oblique grooves, said clamping pins extending via a ring-shaped pressing plate under spring action into an interior of said mount, said clamping pins meshing with a circular ring groove of the first coupling part in a locked position, said clamping pins being displaceable in said oblique grooves against the spring action during insertion of the surgical tool, wherein an actuating slide is pressed in an axial direction by means of said ring-shaped pressing plate by at least one spring into a locked position, said actuating slide being axially displaceable in a release position against the spring force to free the clamping pins from the second coupling part, said pin of said drive meshing with the second coupling part, wherein at least two grooves, whose width and depth correspond to a shape of the pin of said drive, extend at right angles to each other in an end area of the second coupling part, said at least two grooves intersecting with each other, wherein cams formed by milled grooves have edges, each of said edges extending toward said milled grooves and each of said edges being beveled toward said milled grooves to simplify positioning of the second coupling part on the pin of the drive, each of said grooves being defined by two planar parallel extending side walls and a curved bottom wall, said curved bottom wall connecting said two planar parallel extending side walls.

2. A surgical instrument in accordance with claim 1, wherein the surgical tool has a hollow cylindrical tube and said working part located therein with a shaft and with said tool head, wherein the working part is mounted rotatably.

3. A surgical instrument in accordance with claim 2, wherein the first coupling part is arranged proximally at the tube of the surgical tool.

4. A surgical instrument in accordance with claim 1, wherein the handpiece has a grip with said mount for the tool and a locking means within the mount and/or a closing ring is screwed in distally at the handpiece and is closed with an inserted end cap.

5. A surgical instrument in accordance with claim 1, wherein a diameter of the mount is adapted to a diameter of the surgical tool, wherein the first coupling part arranged proximally at the tool is provided with a ring-shaped groove associated with a locking means.

6. A surgical instrument in accordance with claim 1, wherein the first coupling part has a guide slot, which has a shape corresponding to a shape of a rotation prevention means within said mount.

7. A surgical instrument in accordance with claim 1, wherein a ring seal is provided in a closing ring of said handpiece for sealing the mount of the surgical tool and/or a ring seal is provided in said mount for sealing the first coupling part towards the drive shaft.

8. A surgical instrument in accordance with claim 1, wherein the second coupling part is cylindrical with an axial hole, wherein the shaft of the working part is rigidly connected proximally within the axial hole and the second coupling part has radially a through radial hole, which is arranged at right angles to the axial hole and closes the axial hole.

9. A surgical instrument in accordance with claim 1, wherein the second coupling part has such a diameter that a first diameter corresponds to an internal diameter of the shaft of the surgical tool being used and the second coupling part can be inserted into the surgical tool and/or a second diameter of the second coupling part is larger than the first diameter, with a step to the first diameter, which step acts as a stop for the surgical tool and/or a third diameter of the second coupling part is smaller than the first diameter, wherein a seal can be received in a cylindrical recess formed.

10. A surgical instrument in accordance with claim 1, wherein one or more of the first coupling part and the second coupling part have at least one area, which consists of a multiphase plastic, wherein the at least one area contains a copolymer based on methacrylate and styrene, as well as butadiene.

11. A set of surgical tools, comprising:
a surgical instrument for the detachable connection of a handpiece with a surgical tool, the surgical tool comprising:
a tube and a working part with a shaft and a tool head, said tool head being attached to said shaft and said tool head being rotatable with said shaft, wherein the tube of the surgical tool can be detachably connected to the handpiece by means of a first coupling part and wherein the shaft of the working part can be detachably connected to a drive shaft in the form of a pin of a drive of the handpiece by means of a second coupling part simultaneously, wherein a mount in said handpiece receives said first coupling part of the surgical tool, said handpiece comprising two clamping pins displaceable in oblique grooves, said clamping pins extending under spring action into an interior of said mount, said clamping pins being displaceable in said oblique grooves against the spring action during insertion of the surgical tool, wherein an actuating lever is arranged at said handpiece, said actuating lever being pressed by means of a ring-shaped pressing plate with at least one spring, said actuating lever being axially displaceable along an outer edge of said mount between a locked position and a released position, wherein said actuating lever extends along said outer edge of said mount in an axial direction of said surgical instrument, said second coupling part comprising at least two grooves, said at least two grooves being located at an end area of said second coupling part, said second coupling part comprising a first planar side wall portion, a second planar side wall portion, a third planar side wall portion, a fourth planar side wall portion, a first arcuate wall portion and a second arcuate wall portion, said first planar side wall portion being connected to said second planar side wall portion via said first arcuate wall portion, wherein at least said first planar side wall portion, said second planar side wall portion and said first arcuate wall portion define one of said two grooves, said third planar side wall portion being connected to said fourth planar side wall portion via said second arcuate wall portion, wherein at least said third planar side wall portion, said fourth planar side wall portion and said second arcuate wall portion define another one of said two grooves, said one of said at least two grooves extending in a first direction, said another one of said at least two grooves extending in a second direction, said first direction intersecting with said second direction.

12. A set of surgical tools in accordance with claim 11, wherein said pin meshes with the second coupling part, wherein said at least two grooves, whose width and depth correspond to a shape of the pin of said drive, are at right angles to each other in said end area of the second coupling part, wherein said first direction is perpendicular to said second direction, said one of said at least two grooves intersecting with said another one of said at least two grooves, wherein cams formed by milled grooves have edges, each of said edges extending toward said milled grooves and each of said edges being beveled toward said milled grooves to simplify positioning of the second coupling part on the pin of the drive, said actuating lever being movable between said locked position and said released position in a direction parallel to a longitudinal axis of said handpiece.

13. A set of surgical tools in accordance with claim 12, wherein said mount defines at least a portion of said oblique grooves, said at least one spring being arranged in a recess in said mount, said at least two grooves defining a rotatable connection between said pin of said drive and said shaft of said working part, wherein said pin is arranged in one or more of said at least two grooves, at least a portion of said pin being arranged at an intersection of said at least two grooves.

\* \* \* \* \*